United States Patent
Weigl et al.

(10) Patent No.: US 6,974,323 B2
(45) Date of Patent: Dec. 13, 2005

(54) METHOD FOR AUTOMATED PRODUCTION OF CERAMIC DENTAL RESTORATIONS AND PROSTHESES

(75) Inventors: Paul Weigl, Ober-Eschbacher-Strasse 33, D-61352 Bad Homburg, v.d.H (DE); Kristian Werelius, Darmstadt (DE)

(73) Assignee: Paul Weigl, Bad Homburg (DE)

( * ) Notice: Subject to any disclaimer, the term of this patent is extended or adjusted under 35 U.S.C. 154(b) by 7 days.

(21) Appl. No.: 10/412,676

(22) Filed: Apr. 14, 2003

(65) Prior Publication Data

US 2004/0106087 A1 Jun. 3, 2004

(30) Foreign Application Priority Data

Apr. 14, 2002 (DE) ................................ 102 16 590

(51) Int. Cl.[7] ............................ A61C 5/10; B23K 26/00
(52) U.S. Cl. .................................. 433/223; 219/121.72
(58) Field of Search ........................ 433/223; 264/16, 264/19; 219/121.3, 121.67, 121.72

(56) References Cited

U.S. PATENT DOCUMENTS 5,720,894 A 2/1998 Neev et al.

2001/0034010 A1 10/2001 MacDougald et al.
2003/0110862 A1 6/2003 Lubatschowski et al.

FOREIGN PATENT DOCUMENTS

| DE | 196 19 951 A1 | 11/1997 |
| DE | 197 36 110 A1 | 3/1999 |
| EP | 1 013 236 B1 | 6/2000 |
| FR | 2 808 200 | 11/2001 |

*Primary Examiner*—Cary E. O'Connor
(74) *Attorney, Agent, or Firm*—Stites & Harbison PLLC; William E. Jackson

(57) ABSTRACT

The method is used for automated production of dental prostheses in the form of ceramic restorations or ceramic abutments of dental implants, using a computer-controlled laser for shaping by means of removal of material from a ceramic blank. The special feature is that at least one three-dimensionally contoured surface region of the dental prosthesis (4, 8) is machined out of the ceramic blank (3) by means of an ultra-short-pulse laser (1) and shaped into the predetermined shape. Preferably, the ultra-short-pulse laser is first employed in such a way that the great majority of the material to be removed from the ceramic blank is cut off in pieces by the ultra-short-pulse laser, and then the ultra-short-pulse laser need merely vaporize the remainder in an erosive operation.

7 Claims, 1 Drawing Sheet

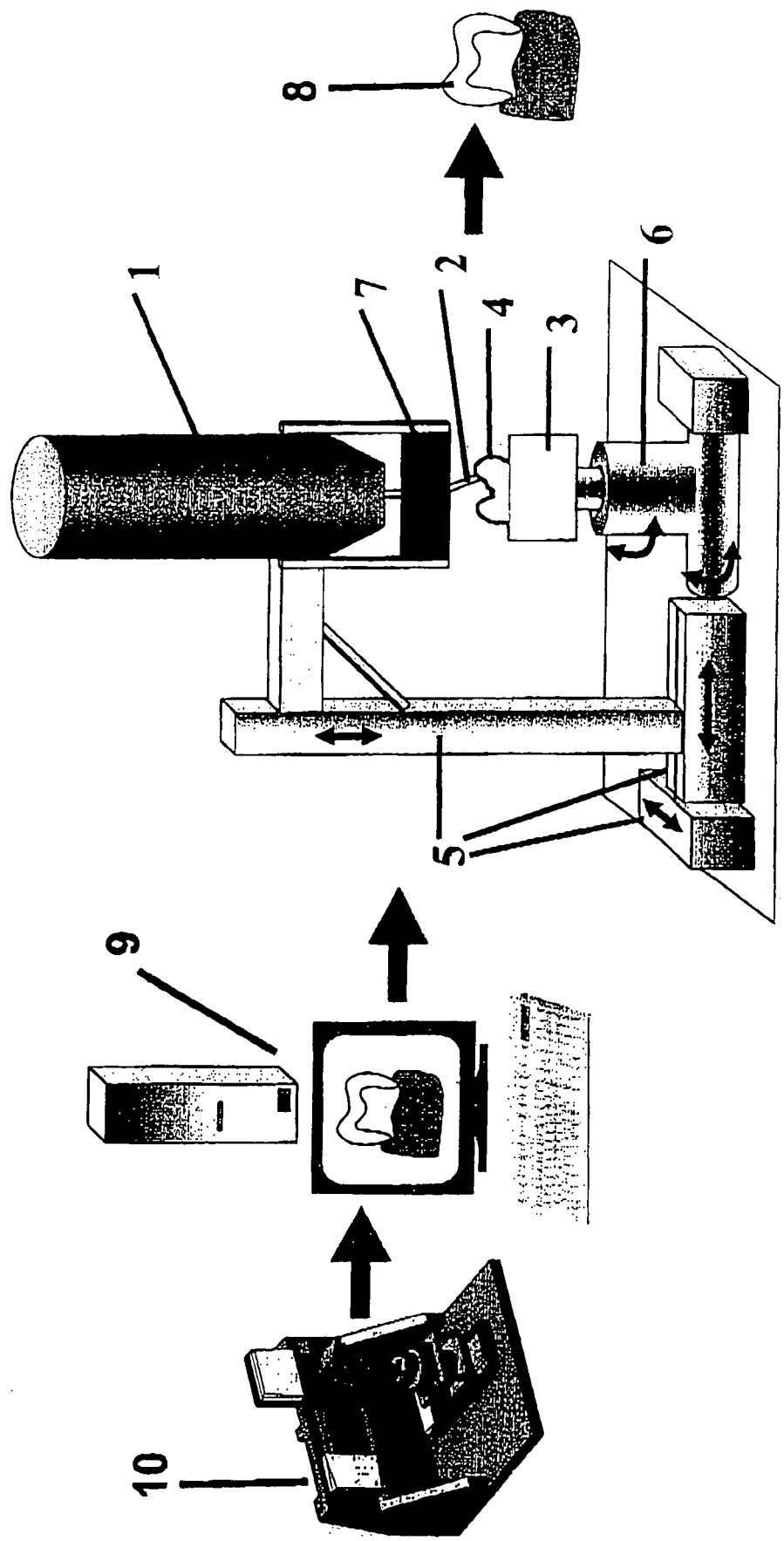

METHOD FOR AUTOMATED PRODUCTION OF CERAMIC DENTAL RESTORATIONS AND PROSTHESES

The invention relates to a method for automated production of dental prostheses in the form of ceramic dental restorations or ceramic, individually formed abutments of dental implants, using a computer-controlled laser for shaping by means of removal of material from a ceramic blank.

There is an urgent need in dentistry for improved therapeutic methods that at the same time reduce costs. Along with prophylaxis, the production by machine of dental restorations in the form of inlay fillings and fixed dental prostheses plays a central role. Another condition for improved, cost-reducing therapeutic methods is to achieve a durable bond between the enamel and dentine of a tooth and restoration materials. This is associated with a significantly longer tooth and prosthesis survival rate in successful therapy, because secondary caries and premature failure of material are decisively limited.

In the restoration of diseased or lost teeth, the natural teeth should be simulated. The highest quality of simulation in terms of strength and appearance can be attained at present by means of ceramic materials. From them, restorations are made in the form of inlay fillings (inlays, onlays, veneers) and fixed dental prostheses (crowns, bridges).

Restorations in which a large majority of the outer surfaces of the tooth to be treated are preserved are generally called dental fillings. Inlay fillings define a subgroup of dental fillings, whose filling material is processed into the desired shape and quality outside the mouth and then is secured, as an integral body, to the tooth. The term "fixed dental prostheses" is used if only very slight portions of the outer surfaces of the teeth, or none, are preserved (crowns), or if a tooth is replaced by the restoration (bridges). Both a fixed dental prosthesis and the inlay fillings are processed into the desired shape and quality solely outside the mouth and are likewise bonded to the tooth using fastening materials. Fixed crowns and bridges are increasingly also being anchored to osseo-integrated implants. The implant component that protrudes into the oral cavity and to which the fixed dental prosthesis is secured is called an abutment. Since the abutment can be individualized in shape outside the mouth, machine-based methods exist for producing individually shaped abutments, especially of ceramic material.

The conventional mode of treatment removes carious tissue using a rotating burr. For receiving an inlay filling, a cavity specific to the restoration material is ground into the tooth, while for receiving a crown, a tooth is prepared conically. The boundary between the ground and the unground tooth substance is defined by a shoulder or tapering chamfer finish line of the preparation. An impression is made of the drilled or ground tooth, so that the inlay filling or the fixed dental prosthesis can be produced on a replica of identical shape. The complex individualized shaping of the restoration is attained by the following methods:

In casting and pressing technology, a wax model of the restoration is modelled manually and embedded in a refractory composition. A molten ceramic is poured or pressed into the hollow mold created. In sintering technology, ceramic powder is applied in layers to refractory replicas or ceramic frameworks of the restoration and built up by means of multiple firings. The final form is achieved by manual removal of material using grinding bodies.

Because of the extensive manual work steps and the requisite casting, pressing or sintering-hardening processes, replicable material quality and production precision of ceramic restorations are not assured.

A more recent production technique for ceramic restorations is computer-controlled shaping using conventional lasers, milling cutters or grinding bodies; see German Patent Disclosure DE 196 19 951 A1. Dental CAx- based production systems can usually be broken down into three components. At the beginning of the process chain, there is a measuring device for acquiring data pertaining to teeth, or restorations of modeling materials, modeled by the dental technician. The measured values for the scanned surfaces form the input data for the second component. In the case of teeth so measured, this component includes CAD-supported construction of the restoration, while in the case of a measured restoration, this component includes processing of the measurement data in a CAD format or CAD-like format. Next, for the inlay filling or fixed dental prosthesis as a component in the CAD system, a control process (CAM) for the shaping NC milling machine is calculated, and this typically represents the third component of the production system.

The many dental CAD/CAM systems available on the market reflect the irreversible trend to industrial production of dental products, especially semifinished products in the form of crown or bridge frameworks, which then has to be manually completed or veneered by a dental technician to make the complete dental prosthesis. The third component of some of the various machine-based production systems for dental restorations will be described briefly below:

For crowns and particularly bridges for molars and bicuspids, ceramics of high strength are needed, so that the chewing forces in this region can be durably withstood. High-strength ceramics, such as HIP-Y-$ZrO_2$TZP (TZP tetragonal zirconia polycrystals; 2 to 3% mol $Y_2O_3$) are used for this purpose as a framework structure (see French Patent Disclosure FR 2 808 200), which is completed by the dental technician using ceramic veneer to make the complete restoration. Because of its strength, HIP-Y-$ZrO_2$(TZP) permits slight layer thicknesses, thus making it possible to prepare canine teeth in a substance-saving way and also to dimension connectors for intermediate bridge members in an esthetically advantageous way. On the other hand, machining HIP-zirconium dioxide in the sintered state (DOS®; cad.asethetics®) requires rigid and hence expensive NC milling machines. Moreover, milling out the restoration from a ceramic blank involves major tool wear and long production times. Both factors stand in the way of economical production, thus reducing the cost of therapy, for restoration components such as frameworks. Because of the grinding body dimensions, there are also limitations in terms of shaping chewing surfaces with fissures in a way that is true to nature. One way out of this problem is to machine $AlO_2$ or $ZrO_2$ in a state in which it is not densely sintered. Between the ceramic particles there is only a material bond by means of organic binders, or weakly defined sintering bridges, and pores make up a high proportion of the volume. Both types of material are so-called green bodies of ceramics. They have a very low strength —similar to chalk —and are easy to machine by grinding. After the grinding shaping of the green bodies, these bodies are densely sintered. The enormous shrinkage, of up to about 30 volume percent, can be compensated for with a CAx system by enlarging the green body geometry. To that end, the geometry of the restoration is enlarged with software support to suit the extent of sintering shrinkage, and the enlarged restoration is milled out of the green body blank using an NC machine. The resultant dimensional errors in this method allow the production only of frameworks for single crowns (Procera®) and bridges (LAVA®; CERCON®), because the high sintering shrinkage does not allow the production of fractal chewing surface geometries with the clinically required precision. On the other hand, the requisite veneering of restoration frameworks that is done by the dental technician to make complete crowns or bridges utilized to correct inaccuracies of fit at the restoration edge of the frameworks by means of the veneering ceramics. Thus the processing of green body ceramics is limited to the production of frameworks.

Economical cutting machining of ceramics becomes possible if one can avoid using material of high mechanical strength. Dental CAD/CAM systems, such as the Cerec® 3-system, use glass ceramics of low mechanical strength that are machined by grinding. However, their indicated use is limited to inlay fillings and individual crowns that do not bear heavy loads. Moreover, the individual crowns in particular require high material layer thicknesses, to counteract the low strength of the glass ceramic. Extensive removal of hard tooth substance threatens the vitality of the tooth, because of the enormous traumatization or opening up of the pulp.

It is true of all the methods described above that at present, there are no available machine-based production processes for ceramics that make high-precision, gentle shaping of restorations with NC milling machines possible. These machines have fit tolerances of up to 300 $\mu$m, and thus do not achieve the clinically required tolerance of below 100 $\mu$m. Because of the oscillations of the milling cutter, it is also impossible to create thin wall thicknesses, for instance of 0.1 to 0.2 mm.

Employing conventional lasers for material-removing production of ceramic dental prostheses has been proposed and attempted, but this has not lead to practical use. In other applications, such as metal machining, lasers are as a rule used only for cutting, drilling or inscribing, but not for shaping a three-dimensionally structured surface that would be comparable to the chewing surface of a tooth by removing material. For this kind of "sculpting" work, the requisite precision of below 100 $\mu$m that is of interest here in the dental field could not be achieved. Moreover, in a surface treatment using conventional laser beam tools (such as Nd:YAG solid-state lasers, excimer lasers, etc.) with pulse lengths in the nanosecond range, unavoidable material damage in the form of melting and cracks would occur at the site of the interaction between the laser and the material. The probability of catastrophic failure of the ceramic would be increased considerably as a result.

The object of the invention is to show another, more advantageous way of producing dental restorations of ceramic, and enlarging their surface area, to increase the strength of bonding with the tooth.

The above object is attained by the method defined by claim 1.

Although ultra-short-pulse lasers have already been known for some time (see DE 197 36 110), it had previously not been thought of that they might be considered for economically shaping ceramic dental prostheses. In comparison to conventional lasers, they do have the advantage of greater precision and of avoiding material damage from the effects of heat, but on the other hand, the removal of material per unit of time is too low. A laser beam of an ultra-short-pulse laser passed over a ceramic surface cuts into the material with a cutting width of only about 30 $\mu$m. Thus the removal capacity in proportion to the volume that must be removed from a ceramic blank in machining out a restoration is so low, and the production time is accordingly so long, that there is apparently no question of using an ultra-short-pulse laser for this application, for reasons of economy.

However, this train of thought is based on experience and on comparison with the other tools used until now for machining dental prostheses out of a ceramic block. Milling cutters, grinding bodies, and conventional lasers in fact have substantially higher material removal capacities. However, this overlooks the fact that an ultra-short-pulse laser can be used with great precision both for removing material and cutting off material, and this distinction has no effect on the mode of operation of the laser but instead affects only what in the CAM method is the computer-controlled guidance of the laser beam relative to the ceramic block. Depending on the particular shape at that instant of the surface at the impact point of the laser beam and its direction, the actions of removing material and of cutting off material merge with one another. By combining the use of cuts for cutting off individual pieces from the ceramic block with a mode of removing material by vaporization to create more-precisely three-dimensionally contoured surfaces, the economy that until now was lacking in the use of a ultra-short-pulse laser can then nevertheless be attained.

In a preferred refinement of the discovery described above on which the invention is based, it is provided that by means of the ultra-short-pulse laser, in a first work step, the great majority of the material to be removed from the ceramic blank in order to machine out the three-dimensionally contoured surface region of the dental prosthesis is cut off in pieces, and the surface of the ceramic blank is approximated to the surface to be produced as the dental prosthesis, and then the remainder of the material present above the surface to be shaped of the dental prosthesis is vaporized by erosive operation of the ultra-short-pulse laser.

As a result of this proposal, most of the ceramic material to be removed is cut off in a time-and energy-saving way, and only a relatively small volume then needs to be removed erosively in order to create the predetermined three-dimensional shape of the dental prosthesis. Since the ultra-short-pulse laser, especially if its pulse length is less than 500 fs, has practically no thermal zone of influence in the ceramic block next to the laser beam meeting it and thus causes no thermal stresses or microscopic cracks, the cuts required for cutting off pieces can already touch the predetermined surface of the restoration to be produced. The ensuing erosive machining with the ultra-short-pulse laser thus likewise makes possible a defined, replicable, burr-free, ultrafine removal of ceramic, without damaging the material in a clinically relevant way. For the production of restorations using the ultra-short-pulse laser, however, an NC-controlled positioning unit is required, which in a defined three-dimensional way moves the focus of the laser beam relative to the material blank, or moves this blank relative to the focus in that way. The positioning unit can have linear axes and rotary axes and/or a galvanometer scanner.

Especially precise removal is achieved by means of a simultaneous distance regulation, in which near the time of, or during, the laser ablation, the distance from the laser to the work piece is measured. From the measured distance taken together with prior distance measurements the material removal can then be determined. Possible measuring methods are described, among other places, in DE 100 20 559 A1; for instance, part of the laser beam can be used not to remove material but instead for measurement purposes. Milling and grinding methods, conversely, lack precision for creating the form of complex chewing surfaces, because of the finite diameters of the milling cutters and grinding bodies. Moreover, because of their vibrations, brittle materials suffer damage that leads to the loss of the initial mechanical strength. Thus it is possible in crown or bridge frameworks to achieve wall thicknesses of less than 0.1 to 0.2 mm only by the method of the invention.

Another advantage of the invention is that with the aid of the ultra-short-pulse laser, in dental restorations of HIP-Y-$ZrO_2$ ceramic, defined micromechanically acting retention patterns can be machined into the later joining surface, in order to achieve a substantially improved adhesive bond with the securing cement.

The method of the invention also makes it simpler to produce individually shaped implant abutments of HIP-Y-$ZrO_2$ ceramic. Once again, a simultaneously machined-in, defined, micromechanically acting retention pattern, which until now had to be milled in accordance with European Patent Disclosure EP 1 013 236 B1, can likewise increase the adhesive bond with securing cements.

One possible application of the method of the invention will be described below as an example in conjunction with the drawing.

BRIEF DESCRIPTION OF THE DRAWINGS

The single FIGURE of the drawing is a schematic of an embodiment of the present invention.

DETAILED DESCRIPTION OF THE DRAWINGS

A three-dimensional measuring unit 10 acquires data from the surface of the prepared tooth, the neighboring teeth, and the opposite tooth from a plaster model which faithfully replicates the intraoral anatomical situation. The measurement data are written into a CAx system 9 and are used as a basis measurement data are written into a CAx system 9 and are used as a basis for the construction of a complete tooth crown with a chewing surface. The inner and outer surfaces of the crown are used to calculate the course of the laser beam in order to machine the crown with the chewing surface 4 out of the HIP-Y-$ZrO_2$ ceramic blank 3. The excess ceramic is ablated or dissolved completely by the ultra-short-pulse laser 1 as follows: First, approaching the form to be produced, as large a volume as possible is cut off in pieces by means of cuts, and then only the remainder is eroded away by the laser beam, burned away without any persistent heat effect on adjacent regions of the material. By means of an NC-controlled positioning unit, for instance with linear axes and/or rotary axes 5 and 6, respectively, and/or with a galvanometer scanner 7, the focus of the laser beam 2 can be moved relative to the material blank 3 in a defined three-dimensional way.

What is claimed is:

1. A method for automated production of dental prostheses in the form of ceramic dental restorations or ceramic, individually formed abutments of dental implants, using a computer-controlled laser for shaping by means of removal of material from a ceramic blank, characterized in that at least one three-dimensionally contoured surface region of the dental prosthesis is machined out of the ceramic blank by means of an ultra-short-pulse laser and shaped into the predetermined shape, wherein by means of the ultra-short-pulse laser, in a first work step, a great majority of the material to be removed from the ceramic blank in order to machine out the three-dimensionally contoured surface region of the dental prosthesis is cut off in pieces, and the surface of the ceramic blank is approximated to the surface to be produced as the dental prosthesis, and then the remainder of the material present above the surface to be shaped of the dental prosthesis is vaporized by erosive operation of the ultra-short-pulse laser.

2. The method of claim 1, wherein a dental prosthesis in the form of a crown or bridge framework is formed with a wall thickness of approximately 0.1 to 0.2 mm on the chewing surfaces and/or the tooth flanks by means of the ultra-short-pulse laser.

3. The method of claim 1, wherein the ultra-short-pulse laser is operated with a pulse length of less than 500 fs.

4. The method of claim 1, wherein the ultra-short-pulse laser is operated with distance regulation, and the measurement of the distance between the laser and the surface of the dental prosthesis being machined at that moment takes place during the machining process.

5. The method of claim 1, wherein high-strength, hot-isostatically pressed, yttrium-doped zirconium dioxide is used as the material of the ceramic block.

6. The method of claim 1, wherein the surfaces of the restoration for securing it to the tooth, or the surfaces of the implant abutment for securing a restoration, undergo an increase in surface area by means of the creation of defined retention patterns with the aid of the ultra-short-pulse laser.

7. The method of claim 1, wherein for the production of restorations or implant abutments by means of an ultra-short-pulse laser, an NC-controlled positioning unit is used, which has linear axes and/or rotary axes and/or a galvanometer scanner, and by which the focus of the laser beam is movable three-dimensionally in a defined way relative to the material blank.

\* \* \* \* \*